United States Patent [19]

Hommann

[11] Patent Number: 5,404,608
[45] Date of Patent: Apr. 11, 1995

[54] ELECTRIC TOOTHBRUSH

[75] Inventor: Edgar Hommann, Grossaffoltern, Switzerland

[73] Assignee: Bausch & Lomb Incorporated, Rochester, N.Y.

[21] Appl. No.: 139,384

[22] Filed: Oct. 19, 1993

[51] Int. Cl.⁶ .................... A61C 17/34; A46B 13/02
[52] U.S. Cl. ................................... 15/22.1; 15/28
[58] Field of Search ............. 15/22.1, 22.2, 28; 74/25, 54, 55

[56] References Cited

U.S. PATENT DOCUMENTS

| | | | |
|---|---|---|---|
| 4,156,620 | 5/1979 | Clemens | 134/6 |
| 4,989,287 | 2/1991 | Scherer | 15/22.1 |
| 5,020,179 | 6/1991 | Scherer | 15/22.1 |

Primary Examiner—Edward L. Roberts, Jr.
Attorney, Agent, or Firm—Salvatore P. Pace; Katherine McGuire

[57] ABSTRACT

An electric toothbrush comprises a handle part (1) and a push-on brush (4). From one end of the handle part (1) there projects the end of a hollow shaft (3) in which a toothbrush arbor (9) is coaxially arranged, the push-on brush (4) being adapted to be pushed on to the hollow shaft (3). The push-on brush (4) has a rotatable tuft of bristles which may be driven by a longitudinally reciprocating connecting rod which attaches to the arbor (9) when the brush (4) and handle (1) are attached together. A gear (18) in the handle part (1) has two cams (23, 27) which are mutually phase shifted by 180. The first cam (23) displaces the hollow shaft (3) and the second cam displaces the toothbrush arbor (9) in the opposite direction.

9 Claims, 3 Drawing Sheets

ELECTRIC TOOTHBRUSH

BACKGROUND OF THE INVENTION

The invention relates to an electric toothbrush with a manually guidable handle part having a motor and a gear, and a push-on brush which is to be fastened thereon and which has a plurality of rotatably arranged bristle holders which each have an eccentric peg engaging in transversely extending grooves in a connecting rod which may be caused to reciprocate in the direction of its longitudinal axis by the gear by means of a toothbrush arbor and a first cam.

U.S. Pat. No. 4,989,287, issued to Scherer on Mar. 5, 1991 and incorporated herein by reference, relates to a toothbrush of this type. With the '287 toothbrush, the push-on brush may be rotatably connected (with respect to its longitudinal axis), by means of a locking connection, onto the front region of the casing of the handle part. The toothbrush arbor and therefore also the connecting rod are caused to oscillate about their longitudinal axis and also to reciprocate in the direction of the longitudinal axis by means of a rocker and a cam engaging therein. The reciprocating movement of the connecting rod is converted into an alternating rotational movement of the tufts of bristles in the brush head of the push-on brush while the oscillating movement of the connecting rod leads to a corresponding oscillating movement of the entire push-on brush.

The drive of the tufts of bristles by a connecting rod leads to problems if the individual tufts of bristles are to be rotated to and fro with a greater angle of rotation. For this purpose, it is necessary to increase the stroke of the connecting rod by increasing the stroke of the toothbrush arbor, and this can give rise to greater eccentricity of the cam of the gear and can therefore lead to an undesirable increase in the size of the gear.

It is known from published PCT International Application No. PCT/EP92/02624 to dispense with the connecting rod for increasing the rotational angle of the tuft of bristles and instead to drive the tufts of bristles by means of a rotatable shaft. However, as toothbrushes with a connecting rod having transverse grooves and eccentric members of the bristle holders engaging therein have proven appropriate, attempts have been mad[e to maintain this principle of production of the alternating rotational movement of the tufts of bristles.

SUMMARY OF THE INVENTION

The object of the invention is to design a toothbrush of the type mentioned at the outset such that a stroke of its connecting rod which is as great as possible may be achieved with a gear which is as compact as possible.

According to the invention, this object is achieved by providing an electric toothbrush comprising a manually guidable handle part having a motor and a gear disposed therein, and a push-on brush having a stem part adapted to be fitted to the handle part. A plurality of rotatably arranged bristle holders, which each have an eccentric peg, are provided on the push-on brush. A connecting rod extends through the stem part and includes at a first end thereof a plurality of transversely extending grooves in each of which an eccentric peg of a respective bristle holder is engaged, said connecting rod being caused to reciprocate in the direction of its longitudinal axis by the gear in the handle by means of a toothbrush arbor and a first cam, wherein the stem part of the push-on brush is adapted to be pushed onto a hollow shaft through which the toothbrush arbor extends and which is displaceably arranged in the handle part. The gear has a second cam which is offset from the first cam by 180° and is attached to the hollow shaft for the simultaneous displacement of the hollow shaft in the direction of the same longitudinal axis as the arbor and connecting rod.

The hollow shaft thus enables the push-on brush to be displaced independently in the direction of its longitudinal axis by displacement of the hollow shaft. In this way, the two cams offset by 180° allow the connecting rod to be moved forwardly when the hollow shaft and therefore the push-on brush move backwardly. A relative movement between the connecting rod and push-on brush thus occurs which, if the eccentricity of the cams is equal, is twice as great as the reciprocating movement of the connecting rod. Owing to the invention, therefore, a large rotational angle of the bristle holders may be achieved with a connecting rod without undesirably great eccentricity being required for this purpose.

The gear in the handle part has a gear wheel which is arranged to be driven by a pinion mounted on the drive shaft of the motor to revolve around an axis of rotation extending transversely to the main direction of the handle part, said gear wheel being designed as a bevel wheel or crown wheel and the first and second cams extending parallel to the axis of rotation of the gear wheel.

The hollow shaft performs an elliptical movement with the push-on brush while the bristle holders with the tufts of bristles rotate in alternate directions of rotation if, according to an advantageous development of the invention, the second cam engages in a receiver in a rocker connected to the hollow shaft in an orientation parallel to the axis of rotation of the gear wheel and the first cam engages in a slot of a link block extending transversely to the toothbrush arbor and rigidly connected to one end thereof.

The electric toothbrush may be guided particularly conveniently and without contortion of the arm if, according to a further development of the invention, the handle part consists of a hand piece and a front piece and if the front piece is designed to pivot to a limited extent relative to the hand piece about a pivot axis aligned with the axis of the gear wheel.

DETAILED DESCRIPTION

Figure 1:
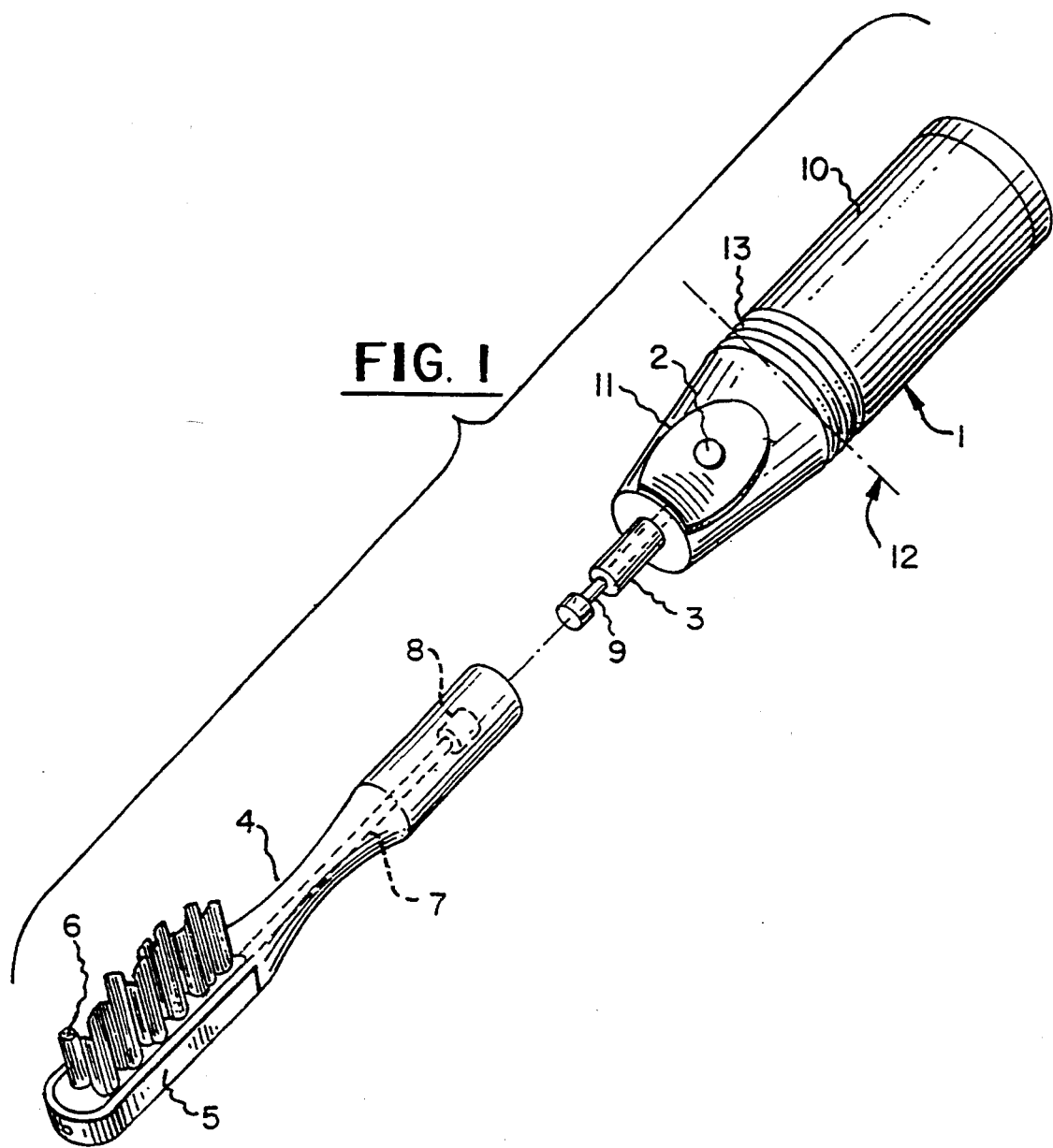
FIG. 1 is a perspective view of one embodiment of a toothbrush according to the invention.

Referring to the drawings, FIG. 1 shows an electric toothbrush in the not yet assembled state with a manually guidable handle part 1 having a switch 2 for switching the electric toothbrush on and off. From the handle part 1 there projects a hollow shaft 3 onto which a push-on brush 4 may be pushed which is held on the hollow shaft 3 by a locking connection (not shown) in the pushed-on state.

The push-on brush 4 has a brush head 5 with a plurality of tufts of bristles 6 arranged rotatably therein. For driving the tuft of bristles 6 there is arranged in the push-on brush 4 a connecting rod 7 which is illustrated in broken lines and which is adapted to be coupled by means of a coupling 8 to a toothbrush arbor 9 arranged coaxially to the hollow shaft 3 in the handle part 1.

The hollow shaft 3 is driven such that it performs an oscillating movement about its longitudinal axis and at the same time reciprocates in the direction of its longitudinal axis. This displacement of the hollow shaft 3 is phase shifted by 180° relative to a reciprocating displacement of the connecting rod 7 also extending in the longitudinal direction.

FIG. 1 shows that the handle part 1 consists of a hand piece 10 and a front piece 11. This front piece 11 is pivotal to a limited extent about a pivot axis 12 extending transversely to the longitudinal axis of the toothbrush. The spacing occurring between hand piece 10 and front piece 11 is compensated by a bellows 13.

Figure 2:
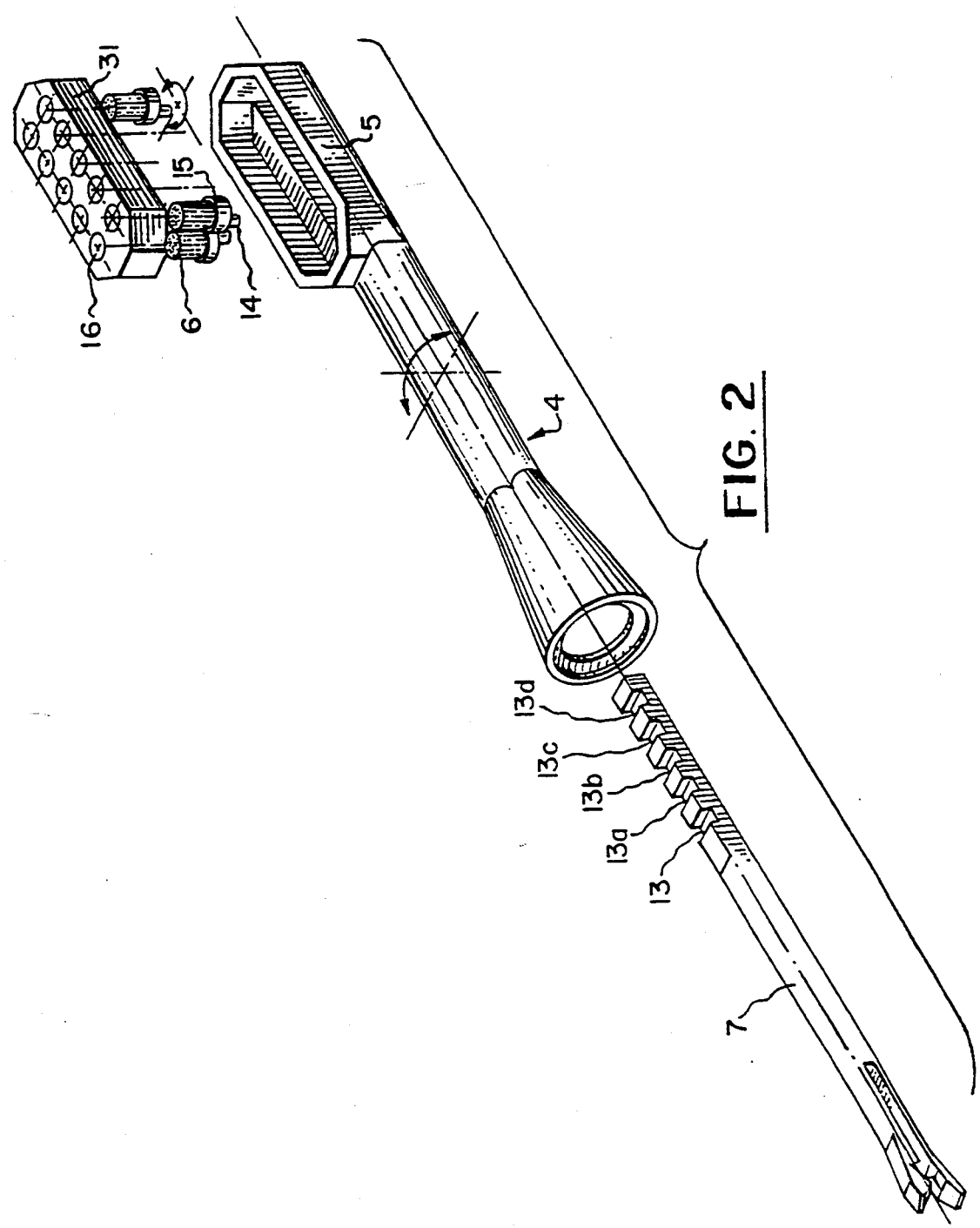
FIG. 2 is an exploded perspective view of the push-on brush part of the toothbrush shown in FIG. 1.

FIG. 2 shows how a rotational movement is produced from a reciprocating movement by means of the connecting rod 7. This part of the electric toothbrush shown in FIG. 2 corresponds completely to that in the '287 patent. It can be seen that the connecting rod 7 has a total of five transversely extending grooves 13, 13a, 13b, 13c, 13d which are arranged in longitudinally spaced succession at its brush head end and into which there engage eccentric pegs 14 projecting from bristle holders 15 holding the tufts of bristles 6. The bristle holders 15 may be inserted from below into holes 16 in an insert 31 which, in turn, is held in the brush head 5.

Figure 3:
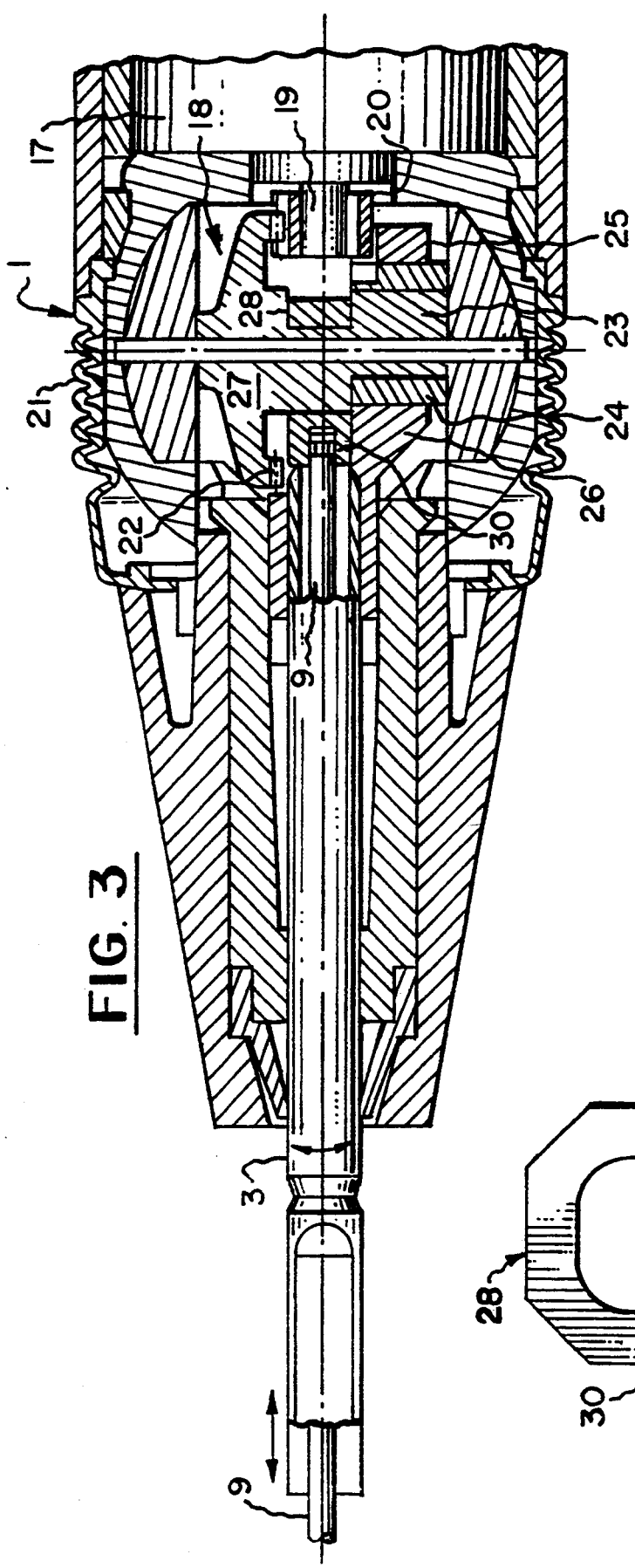
FIG. 3 is a longitudinal section through the gear region of the toothbrush.
Figure 4:
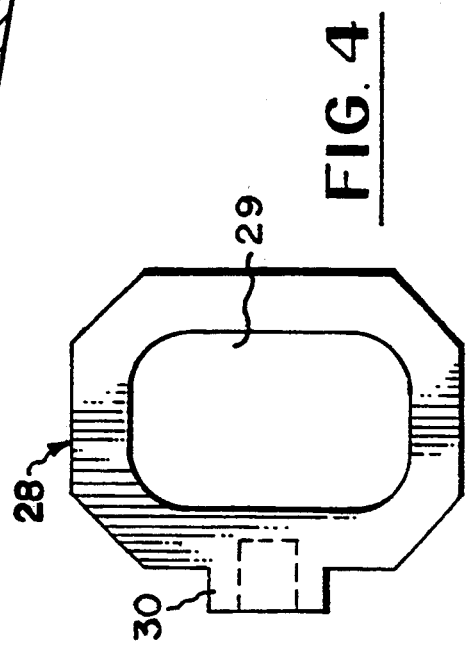
FIG. 4 is a plan view of a link block of the gear.

FIG. 3 shows a section through a front region of the handle part 1 with a motor 17 which is arranged to drive the hollow shaft 3 and the toothbrush arbor 9 via a gear 18. The motor 17 has a motor shaft 19 with a pinion 20. The pinion 20 continuously drives a gear wheel 22 which is rotatably mounted on a shaft 21 which in turn is fixedly mounted in the handle part and extends transversely to the longitudinal axis of the said handle part 1, the gear wheel 22 being designed as a bevel wheel or crown wheel. The gear wheel 22 has a first cam 27 which is phase-shifted by 180° relative to a second cam 23 described more fully below. A link block 28, the design of which is shown in FIG. 4, has a link guide 29 which extends transversely to the longitudinal axis of the hollow shaft 3 and in which the first cam 27 shown in FIG. 3 engages. The link block 28 has, on the side of the toothbrush arbor 9, a peg 30 which is also shown in FIG. 3 and in which one end of the toothbrush arbor 9 engages.

Second cam 23, which engages in a sliding block 24 of a rocker 25, is provided parallel to the gear or cam axis defined by shaft 21 on the gear wheel 22. The rocker 25 extends parallel to the hollow shaft 3 and is rigidly connected to it by a radial connecting piece 26. The shaft 21 simultaneously forms the pivot axis 12 shown in FIG. 1. The exact configuration of this part of the gear 18, which is to be called a push/rock type gear, is described in the above-mentioned '287 patent. The hollow shaft 3 thus performs an elliptical movement owing to the known push/rock type gear.

When the gear wheel 22 rotates, the first cam 27 causes the link block 28 to reciprocate in the longitudinal direction of the toothbrush so the toothbrush arbor 9 performs a corresponding displacement. At the same time, the second cam 23, which is phase shifted by 180° relative to first cam 27, causes the hollow shaft 3 to reciprocate so that a relative movement takes place between the hollow shaft 3 (and therefore also the toothbrush head 5) and the arbor 9 (and thus also the connecting rod 7) which corresponds to the sum of the eccentricities of the two cams 23, 27. As such, a large rotational displacement (i.e., substantially 180°) of the bristle holders 15 in a single direction is generated through the combined, directionally opposite, linear displacements of the brush head 5 and connecting rod 7.

I claim:

1. In an electric toothbrush having separable handle and slip-on brush segments extending along first and second longitudinal axes, respectively, said handle component having a motor with a revolving motor shaft, said slip-on brush having an open, proximal end and a distal end having a brush head with at least one bristle tuft mounted for counter-rotating movement thereon, said slip-on brush further having a reciprocal connecting rod having first and second ends disposed therein and extending parallel to said second longitudinal axis, said connecting rod being connected at said first end thereof to said at least one bristle tuft for imparting said counter-rotating movement thereto through the reciprocating movement of said connecting rod, wherein the improvement comprises:

a) an elongated arbor having first and second ends disposed within said handle segment;

b) means removably attaching said arbor first end to said connecting rod second end in colinear relationship thereto upon said slip-on brush and handle segments being attached together;

c) a hollow shaft having first and second ends disposed within said handle segment in outwardly telescoping, coaxial relation to said arbor, said slip-on brush open end attaching to said hollow shaft first end upon said slip-on brush and handle segments being attached together, said arbor and hollow shaft being movable independently of each other parallel to said first longitudinal axis;

d) first cam means rotatably mounted within said handle segment about a cam axis which lies substantially perpendicular to said first longitudinal axis, said first cam means connected to said arbor second end and operable through said motor shaft to impart a reciprocating movement to said arbor and said connecting rod which imparts said counter-rotating movement to said at least one tuft; and e) second cam means rotatably mounted in said handle segment, said second cam means longitudinally and annularly spaced substantially about 180° from said first cam means about said cam axis, said second cam means being connected to said hollow shaft second end and operable through said motor shaft to impart a reciprocating movement to said hollow shaft and said slip-on brush segment, said reciprocating movement of said arbor and said connecting rod being simultaneous with and in a direction opposite to the reciprocating movement of said hollow shaft and said slip-on brush segment whereby the total rotational movement of said at least one bristle tuft in a single direction substantially equals the combined radial displacements of said first and second cam means from said cam axis.

2. The electric toothbrush according to claim 1 wherein the improvement further comprises:

f) rocker means attached between said second cam means and said hollow shaft, said rocker means being operable to impart an elliptical movement to said hollow shaft and said slip-on brush through the rotation of said second cam means about said cam axis.

3. The electric toothbrush of claim 2 wherein said handle segment includes a flexible portion wherethrough said cam axis extends.

4. The electric toothbrush according to claim 2 wherein said rocker means comprises a rocker having a rectangular opening and a rectangular sliding block disposed in said opening, said sliding block having a central bore wherein said second cam means is rotatably positioned, said sliding block further having opposite, beveled surfaces lying in abutting relationship to respective opposite surfaces of said rocker opening.

5. The electric toothbrush according to claim 4 and further comprising a radial connecting piece interconnecting said hollow shaft second end and said rocker.

6. The electric toothbrush according to claim 1 wherein the improvement further comprises a bevel gear rotatably mounted in said handle segment about said cam axis in meshing engagement with a pinion of said motor shaft, said first and second cam means being fixedly attached to and rotatable with said bevel gear.

7. The electric toothbrush according to claim 1 wherein said first longitudinal axis extends through said first cam means.

8. The electric toothbrush according to claim 1 wherein said brush head includes a plurality of said bristle tufts with each said bristle tuft being secured to a respective bristle carrier having an eccentric peg, and further comprising a plurality of spaced, parallel grooves formed in said connecting rod first end, said grooves extending transversely to said connecting rod substantially perpendicular to said second longitudinal axis, each of said eccentric pegs of said bristle carriers being engaged in one of said grooves.

9. The electric toothbrush according to claim 1 and further comprising a link block interconnecting said arbor second end to said first cam means, said link block having an elongated opening extending substantially parallel to said cam axis, said first cam means being freely rotatably positioned in said elongated opening.

* * * * *

UNITED STATES PATENT AND TRADEMARK OFFICE
CERTIFICATE OF CORRECTION

PATENT NO. : 5,404,608
DATED : April 11, 1995
INVENTOR(S) : Edgar Hommann

It is certified that error appears in the above-indentified patent and that said Letters Patent is hereby corrected as shown below:

Title page, item [57], col. 2,

In the abstract, line 11, change "180" to -- 180° --.

In column 1, line 14, change "Mar. 5" to -- Feb. 5 --.

In column 1, line 46, change "mad[e" to -- made --.

Signed and Sealed this

Twenty-fourth Day of October, 1995

Attest:

BRUCE LEHMAN

*Attesting Officer*  *Commissioner of Patents and Trademarks*